United States Patent
Kiyooka et al.

(10) Patent No.: US 6,700,003 B2
(45) Date of Patent: Mar. 2, 2004

(54) PROCESS FOR PRODUCING A SATURATED CYCLIC ETHER

(75) Inventors: Kazuhiko Kiyooka, Kanagawa (JP); Toshiharu Yokoyama, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/316,937

(22) Filed: Dec. 12, 2002

(65) Prior Publication Data

US 2003/0149282 A1 Aug. 7, 2003

Related U.S. Application Data

(63) Continuation of application No. PCT/JP01/05032, filed on Jun. 13, 2001.

(30) Foreign Application Priority Data

Jun. 13, 2000 (JP) ........................................ 2000-176303
Jun. 23, 2000 (JP) ........................................ 2000-189193

(51) Int. Cl.[7] ............................................ C07D 307/02
(52) U.S. Cl. ...................................... 549/508; 549/509
(58) Field of Search ................................ 549/508, 509

(56) References Cited

U.S. PATENT DOCUMENTS 4,005,113 A * 1/1977 Smith .......................... 549/508
4,079,068 A * 3/1978 Hetzel et al. ................ 549/508

FOREIGN PATENT DOCUMENTS

| JP | 51-41351 | 4/1976 |
| JP | 51-76264 | 7/1976 |
| JP | 2000-178213 | 6/2000 |

OTHER PUBLICATIONS

References Not Supplied as They are the US Equivalents to JP 51–76264 and JP 51–41351 (Supplied by Applicant) Respectively.*

* cited by examiner

Primary Examiner—Amelia Owens
(74) Attorney, Agent, or Firm—Oblon, Spivak, McClelland, Maier & Neustadt, P.C.

(57) ABSTRACT

A method for producing a saturated cyclic ether from a fatty acid ester of an $\alpha$, $\delta$-diol stably in high yield over a long period of time, is presented. It is a process for producing a saturated cyclic ether, which comprises reacting a mono- and/or di-fatty acid ester of an $\alpha$, $\delta$-diol in the presence of a solid acid catalyst, wherein the reaction is carried out in such a state that at least 50 mol % of the fatty acid ester supplied to the reaction system is vaporized.

15 Claims, No Drawings

PROCESS FOR PRODUCING A SATURATED CYCLIC ETHER

This application is a Continuation of international Application No. PCT/JP01/650321, filed Jun. 13, 2001.

TECHNICAL FIELD

The present invention relates to a process for producing a saturated cyclic ether. Particularly, it relates to a process for producing a saturated cyclic ether such as tetrahydrofuran, which comprises reacting a mono- and/or di-fatty acid ester of an α, δ-diol in the presence of a solid acid catalyst.

BACKGROUND ART

A saturated cyclic ether such as tetrahydrofuran is a compound which is extremely useful as an organic solvent, or as a raw material for e.g. polytetramethylene ether glycol.

As a method for producing tetrahydrofuran, a method of hydrogenating butynediol made from acetylene and formaldehyde to convert it to butanediol, followed by dehydration cyclization, or a method of reacting an acetic acid ester of 1,4-butanediol with water in the presence of an acid catalyst, has, for example, been known.

As the acid catalyst, it is known to employ a liquid acid or a solid acid. As a method of using a liquid acid, a method of carrying out the reaction in a liquid phase by using sulfuric acid, is known (JP-A-52-93762, corresponding U.S. Pat. No. 4,105,679). With respect to a method of using a solid acid, as the reaction method, a method wherein the reaction is carried out by liquid/liquid contact of all substrates in a liquid phase (JP-A-52-7909) or a method wherein the reaction is carried out by gas/liquid contact with an ester in a liquid phase and with water in a gas phase (JP-A-52-95655, JP-A-52-95656), is known.

However, such conventional methods have had some problems. Firstly, in the case of a method of using sulfuric acid as the catalyst, a high concentration sulfuric acid is employed, whereby coloration of the reaction liquid tends to be substantial, and separation from the reaction product tends to be difficult. Further, corrosion of the reactor by sulfuric acid is substantial, and the yield is also low.

Also in the case of using a solid acid catalyst, the conventional methods were carried out by a liquid phase reaction by liquid/liquid contact or by a gas liquid mixed reaction by gas/liquid contact. For example, in JP-A-52-95655 or in JP-A-52-95656, a liquid acetic acid ester and steam were reacted to produce a cyclic ether. In these conventional methods, at least an ester as one of substrates is present entirely in a liquid phase in the reaction system, whereby there have been the following problems.

① Due to clogging of the catalyst, deterioration in the activity will occur.

② A liquid is adsorbed on the surface of the catalyst, whereby the flow rate control or the contact time control tends to be difficult.

③ The mixing is not uniform, whereby there will be a portion where the concentration of the ester is locally high, thus leading to deterioration in the activity or an increase of a side reaction.

④ The catalyst component will dissolve in a liquid phase carboxylic acid desorbed under a high temperature condition, whereby deterioration in the activity and in the useful life of the catalyst will result.

It is an object of the present invention to solve such problems of the prior art and to provide a process for producing a saturated cyclic ether such as tetrahydrofuran stably in high yield over a long period of time, by reacting a fatty acid ester of an α, δ-diol such as 1,4-butanediol in the presence of a solid acid catalyst.

DISCLOSURE OF THE INVENTION

The present inventors have conducted an extensive study under such circumstances and as a result, have found that in the production of a saturated cyclic ether such as tetrahydrofuran by reacting a fatty acid ester of an α, δ-diol such as 1,4-butanediol in the presence of a solid acid catalyst, the above-described problems can be all solved by reacting the fatty acid ester in such a state that at least 50 mol %, preferably substantially all of the fatty acid ester as the reaction substrate, is in a vaporized gas phase state, and thus have completed the present invention.

According to the process of the present invention, as compared with the case of the conventional liquid phase reaction or the gas/liquid contact reaction, the reaction can be carried out within a wide temperature range from a low temperature to a high temperature, formation of by-products is little, and the flow rate control and the contact time control are easy. Further, even by a high temperature reaction or a reaction for a long time, deterioration of the catalyst is less, and even if the amount of water to be supplied, is reduced, the reaction proceeds completely, and the load in the subsequent separation of water can be reduced. Further, deterioration of the catalyst due to a carboxylic acid formed during the reaction will be low as compared with the gas/liquid contact reaction or the liquid phase reaction. Further, as compared with the gas/liquid contact reaction, in the gas phase reaction, the fatty acid ester and water are uniformly dispersed, whereby the reaction efficiency is good, and the yield will be high, and formation of by-products can be suppressed.

Namely, the gist of the present invention resides in a process for producing a saturated cyclic ether, which comprises reacting a mono- and/or di-fatty acid ester of an α, δ-diol in the presence of a solid acid catalyst, wherein the reaction is carried out in such a state that at least 50 mol % of the fatty acid ester supplied to the reaction system is vaporized.

BEST MODE FOR CARRYING OUT THE INVENTION

Now, the present invention will be described in detail.

In the present invention, the condition that the reaction is carried out in such a state that at least 50 mol % of the fatty acid ester as the reaction substrate supplied to the reaction system, is vaporized, will vary variously depending upon the reaction substrate, the reaction temperature, the reaction pressure and the amount of the inert substance added. However, it is necessary to satisfy the following two points (1) and (2).

(1) In a case where all of the reaction substrates introduced, are gas, the reaction is carried out under such a condition that the molar ratio of raw material components to be introduced into the reaction system, and the saturated vapor pressure of the fatty acid ester at the reaction temperature under the reaction pressure, satisfy the following relation:

(mols corresponding to x mol % of the fatty acid ester/total mols of all materials)<(saturated vapor pressure of the fatty acid ester at the reaction temperature under the reaction pressure/ reaction pressure)

where all materials mean the fatty acid ester, water and gaseous inert components, and x represents the vaporized ratio (mol %) of the fatty acid ester supplied to the reaction system.

In the present invention, the vaporized ratio x is 50 mol %.

(2) In a case where the reaction substrates introduced are liquid even partly, it is necessary not only to satisfy the requirement of the above (1), but also to apply, in addition to the calory required to bring all water introduced, to the reaction temperature and to vaporize it, the calory required to bring the ester introduced, to the reaction temperature and to vaporize at least x mol % thereof, after the introduction of the substrates and before the substrates contact the catalyst.

With respect to the above (1) and (2), in the present invention, the vaporized ratio x is at least 50 mol %.

Here, the calory required for vaporization is determined by considering the method for heating the reactor and conditions such as the thermal conductivity of the material of the reactor, the supplied amount of the calory (per unit time), and the space, volume, etc. until the reaction substrates will contact the catalyst in the reactor.

In the present invention, by adding a gaseous inert component to the reaction system, it is possible to reduce the partial pressure of the fatty acid ester and to facilitate vaporization of the reaction substrate within wider reaction temperature and reaction pressure ranges. Such an inert component is not particularly limited. For example, nitrogen, carbon dioxide, argon, air or oxygen may be employed, and preferably, nitrogen, carbon dioxide or air may be employed.

As an example, a case may be mentioned in which 1,4-diacetoxybutane (hereinafter referred to as DAB) and water are used as reaction substrates, and the reaction is carried out under normal pressure to form tetrahydrofuran. In such a case, the boiling point of DAB is highest at 223° C. among the reaction substrates. Accordingly, if the reaction temperature is higher than 223° C., all substrates (DAB, water, tetrahydrofuran, acetic acid) will be in a gas phase state, and therefore, there will be no problem. Further, in a case where the reaction temperature is 120° C., and the reaction substrates are introduced at 120° C. (water is gas, and DAB is liquid), as the saturated vapor pressure of DAB is about 20 mmHg, if the molar ratio of the raw materials introduced is DAB/all materials<1/20 (where 1/20 is determined by (20/760) mmHg÷0.5, and all materials mean DAB+water+gaseous inert components), at least 50 mol % can be vaporized, and thus it is simply required to satisfy this condition, and to apply a calory required to vaporize at least 50 mol % of DAB as a reaction substrate, to the reaction system after introducing the substrate.

Likewise, in a case where the reaction temperature is 180° C., and the reaction substrates are introduced at 180° C. (water is gas, DAB is liquid), and for example, at least 50 mol % of DAB as a reaction substrate is to be vaporized, as the saturation vapor pressure of DAB at 180° C. is about 200 mmHg, if the molar ratio of the raw materials introduced is DAB/all materials<1/2 (where 1/2 is determined by (200/760) mmHg÷0.5, and all materials mean DAB+water+gaseous inert components), at least 50 mol % can be vaporized, and it is simply required to satisfy this condition, and to apply a calory required to vaporize at least 50 mol % of DAB as a reaction substrate, from the introduction of the substrate and before the substrate is in contact with the catalyst.

In a case where the substrates, the reaction temperature, the reaction pressure and the amount of the gaseous inert component to be added, are different, the conditions may be defined in accordance with the above cases, and it is possible to adjust the vaporized ratio x (mol %) of the fatty acid ester by changing the conditions within wide ranges. Further, with respect to the fatty acid ester as a reaction substrate, at least 50 mol % of the fatty acid ester supplied to the reaction system may be vaporized, and there is no restriction as to the temperature at the time of its introduction. Further, all or a part of the fatty acid ester may be introduced as a gas, or a part or all of the fatty acid ester may be introduced as a liquid and heated in a reaction tube or a pre-heater, to make at least 50 mol % of the fatty acid ester to be a gas.

When at least 50 mol % of the ester is in a gas phase state, the contribution of the gas phase reaction tends to be larger, whereby the present invention will be effective. The larger the proportion (x mol %) of the gas phase state of the raw material ester supplied, the larger the effect. It is preferred to carry out the reaction in such a state that at least 60 mol %, more preferably at least 70 mol %, further preferably at least 80 mol %, particularly preferably substantially all i.e. at least 90 mol % of the fatty acid ester, is vaporized. Most preferably 100 mol % of the raw material ester is in a gas phase state. Accordingly, also with respect to the above-mentioned requirement (1) to accomplish the present invention, it is possible to select the conditions so that the vaporized ratio (x) of the ester will be such a preferred ratio.

Further, in the present invention, it is preferred to supply the fatty acid ester preliminarily vaporized in an amount of at least 50 mol %, and it is more preferred to supply it to the reaction system in such a state that at least 60 mol %, more preferably at least 70 mol % particularly preferably at least 80 mol %, most preferably substantially all i.e. at least 90% of the fatty acid ester, is vaporized.

The α, δ-diol in the present invention may be any compound so long as it is a compound having two carbon atoms between two carbon atoms having hydroxyl groups substituted, and it may further have a substituent such as an alkyl group, an alkoxy group or an aryl group. Among them, an alkanediol is preferred, and 1,4-butanediol is particularly preferred.

The mono- and/or di-fatty acid ester of the α, δ-diol, to be used in the present invention, is not particularly limited, but it is preferably a diester. Among them, an ester of a saturated fatty acid having from 2 to 4 carbon atoms is preferred, and an acetic acid ester is particularly preferred. Further, the raw material ester may contain 1,4-butanediol or other alcohols or esters, as impurities, so long as they are not compounds adversely affect the reaction and their content is not so large.

In the present invention, a saturated cyclic ether is produced from the mono- and/or di-fatty acid ester of the α, δ-diol. Here, the saturated cyclic ether is a compound wherein the ring structure forming the cyclic ether has no unsaturated bond, and the ether ring may further have the above-mentioned substituent such as an alkyl group, an alkoxy group or an aryl group, and may have a substituent having an unsaturated bond. As the saturated cyclic ether, tetrahydrofuran is particularly preferred.

The molar ratio for introduction of raw materials carried out in the present invention may be varied within a wide range so long as the above-mentioned gas phase state of the present invention can be maintained. However, the molar ratio of the raw material ester/all materials is preferably from 0.01 to 1, more preferably from 0.03 to 1, particularly preferably from 0.05 to 1.

As the catalyst to be used in the present invention, a solid acid catalyst showing either a Bronsted acidity or Lewis acidity in the reaction system can be used. Specifically, a zeolite having a crystal structure of X, Y or MFI, or a mesoporous body such as MCM-41 or FSM-16 having a one dimensional mesopore tunnel structure or one having a metal atom such as Ti, Al or Zr incorporated in such a structure, a metal oxide such as silica, alumina, titania or zirconia, a compound oxide having a plurality of metal oxides combined, such as silica/titania, silica/alumina or alumina/titania, and further, a supported type acid catalyst obtained by having a compound with an acidic nature such as $H_2SO_4$ or heteropoly acid supported on such an oxide or activated carbon as a carrier, may, for example, be mentioned. Further, it is possible to use a cation exchange resin having acidic functional groups or a solid Bronsted acid such as naphione. Among them, a single metal oxide such as alumina, zirconia or titania, a hydrous metal oxide such as niobic acid, or a mixed oxide such as titania/silica or zirconia/silica, is preferred, and particularly preferred is zirconia or niobic acid.

The reaction of the present invention can be carried out by any of a batch process, a semi-batch process or a continuous process in the same manner as a conventional method, but it is advantageous to carry out the reaction by a continuous system.

The supply velocity (LHSV) of the fatty acid ester of 1,4-butanediol per unit volume of the catalyst, can be changed within a wide range, but it is usually from 0.01 to 1,000 $hr^{-1}$, preferably from 0.05 to 500 $hr^{-1}$, more preferably from 0.1 to 100 $hr^{-1}$. The amount of water to be used in this reaction is not particularly limited, but it is usually from 0.01 to 100 times, preferably from 0.1 to 50 times, more preferably from 0.3 to 20 times, particularly preferably from 0.5 to 15 times, by a molar ratio, to the fatty acid ester of 1,4-butanediol.

According to the present invention, as compared with a conventional catalyst, even in a case of a small amount of water (in a case where a difatty acid ester of an α, δ-diol is used as the raw material, an amount of 1 time by mol to the minimum amount of the diacetic acid ester required for complete reaction), specifically in a case of at most 5 times by mol, preferably at most 3 times by mol, to the amount of the fatty acid ester supplied, tetrahydrofuran can be produced easily at a high conversion and with high selectivity. Further, water remaining after the reaction can thereby be minimized, and the load for the subsequent separation between the product and water, can be reduced. Further, in a case where a fatty acid ester of the α, δ-diol as the raw material is entirely monoester, the reaction can be proceeded completely without using water. Further, in a case where the fatty acid ester of 1,4-butanediol is a mixture of a monoester and a di-ester, the minimum amount of water required to let the reaction proceed completely, is an amount of 1 time by mol to the contained diester. In the present invention, when the reaction is carried out in the presence of water, it is preferred to carry out the reaction in such a state that the fatty acid ester as a reaction substrate, and water are substantially entirely vaporized.

The water to be used in the present invention is not particularly limited, and water separated and recovered after the reaction may be re-used. In the case of such re-use, it is possible to use water containing a small amount of a fatty acid such as acetic acid, an alcohol such as 1,4-butanediol or an ester such as the raw material ester, so long as it is not a compound which substantially adversely affect the reaction.

The temperature for the reaction in the present invention may be within a wide range, but it is usually from 180 to 350° C., preferably from 190 to 330° C., more preferably from 200 to 300° C. Even in a high temperature reaction, according to the process of the present invention wherein reaction is carried out in such a state that at least 50 mol % of the ester as a reaction substrate is in a gas phase state, there is no substantial increase of by-products or no substantial deterioration of the catalyst, whereby the reaction can be carried out at a high temperature which is advantageous from the viewpoint of the reaction rate. In the present invention, it is more preferred to carry out the reaction at a reaction temperature higher than the boiling point of the fatty acid ester under the pressure of the actual reaction.

The pressure in the present reaction is not particularly limited, but it is usually within a range of from 0.01 to 1 MPa, preferably from 0.03 to 0.8 MPa, more preferably from 0.05 to 0.5 MPa.

With respect to the saturated cyclic ether such as crude tetrahydrofuran thus obtained, in a case where the raw material is 1,4-diacetoxybutane, 1,4-diacetoxybutane as the unreacted raw material, acetic acid, water, etc., may be separated and purified by distillation. The separated raw material such as 1,4-diacetoxybutane, may be recycled to the reaction system.

EXAMPLES

Now, the present invention will be described in further detail with reference to Examples. However, the present invention is by no means restricted to such Examples. In the following Examples, 1,4-DAB represents 1,4-diacetoxybutane, and THF represents tetrahydrofuran. Further, hereinafter, "%" represents "mol %", and the conversion and the selectivity were obtained as follows.

Conversion (1,4-DAB)=(mols of reacted 1,4-DAB/mols of 1,4-DAB supplied)×100 (%)

Selectivity (tetrahydrofuran)=(mols of formed tetrahydrofuran/mols of 1,4-DAB reacted)×100 (%)

Although no accurate calculation can be carried out since it is difficult to measure the calory by the reaction apparatus employed in Examples and Comparative Examples this time, it is considered that the raw material esters reached a gas/liquid equilibrium state at the respective reaction temperatures, since a sufficient pre-heating space was present (from 8 to 40 times to the catalyst layer) from the introduction of the reaction substrate until the substrates contacted the catalyst layer, under the conditions of Examples and Comparative Examples. In Examples 1 to 15, the reaction substrates are all in a gas phase state when they reach the catalyst layer, since these Examples are under a condition such that even when the esters are all vaporized, the pressure is not higher than the saturated vapor pressure at that reaction temperature. On the other hand, in Examples 16 and 17, the reaction substrates are in a gas/liquid equilibrium state at the reaction temperature, when the reaction substrates reach the catalyst layer.

Example 1

8.14 mmol/hr of 1,4-diacetoxybutane (1,4-DAB), 9.92 mmol/hr of water (water/1,4-DAB=1.2), and 1.35 l/hr of nitrogen were supplied to a cylindrical reactor made of glass having a diameter of 17 mm and a length of 18 cm and maintained at 240° C. To the reactor, 1 ml (0.95 g) of niobic acid ($Nb_2O_5 \cdot nH_2O$, manufactured by CBMM Company, niobium hydroxide was calcined at 300° C. for two hours, the temperature raising speed: 2.5° C./min, SA: 121 $m^2/g$) was packed and on the top of the catalyst layer, SUS particles were packed. A formed liquid obtained from the bottom of the reactor was analyzed by GC to obtain the following results (in all of the following analyses, GC was used.).

| Conversion (1,4-diacetoxybutane) | 90.8% |
| Selectivity (tetrahydrofuran) | 99.3% |

Example 2

A reaction was carried out in the same manner as in Example 1 except that the amount of water supplied was changed to 74.1 mmol/hr (water/1,4-DAB=9), niobic acid as the catalyst was changed to 3 ml (2.12 g), and the reaction temperature was changed to 200° C., and the formed liquid was analyzed in the same manner to obtain the following results.

| Conversion (1,4-diacetoxybutane) | 100.0% |
| Selectivity (tetrahydrofuran) | 99.9% |

Example 3

A reaction was carried out in the same manner as in Example 1 except that 4 ml (5.16 g) of zirconia (manufactured by Norton Company, SA: 335 m$^2$/g) was used as a catalyst, and the reaction temperature was changed to 280° C., and the formed liquid was analyzed in the same manner to obtain the following results.

| Conversion (1,4-diacetoxybutane) | 99.9% |
| Selectivity (tetrahydrofuran) | 99.9% |

Example 4

A reaction was carried out in the same manner as in Example 1 except that 3 ml (3.68 g) of zirconia (manufactured by Norton Company, SA: 335 m$^2$/g) was used as a catalyst, and the amount of 1,4-DAB supplied was changed to 3.46 mmol/hr, and the amount of water supplied was changed to 9.92 mmol/hr (water/DAB=3), and the reaction temperature was changed to 260° C., and the formed liquid was analyzed in the same manner to obtain the following results.

| Conversion (1,4-diacetoxybutane) | 97.7% |
| Selectivity (tetrahydrofuran) | 99.6% |

Example 5

A reaction was carried out in the same manner as in Example 1 except that 10 ml (10.26 g) of zirconia (manufactured by Norton Company, SA: 106 m$^2$/g) was used as a catalyst, and the reaction temperature was changed to 260° C., and the formed liquid was analyzed in the same manner to obtain the following results.

| Conversion (1,4-diacetoxybutane) | 96.0% |
| Selectivity (tetrahydrofuran) | 99.9% |

Example 6

A reaction was carried out in the same manner as in Example 1 except that 5 ml (4.83 g) of zirconia (manufactured by Norton Company, SA: 106 m$^2$/g) was used as a catalyst, the amount of 1,4-DAB supplied was changed to 3.42 mmol/hr (water/DAB=3), and the reaction temperature was changed to 260° C., and the formed liquid was analyzed in the same manner to obtain the following results.

| Conversion (1,4-diacetoxybutane) | 95.5% |
| Selectivity (tetrahydrofuran) | 96.1% |

Example 7

A reaction was carried out in the same manner as in Example 1 except that 3 ml (1.41 g) of silica/alumina (manufactured by JGC Corporation, $Sio_2$: 65–70 wt %, $Al_2O_3$: 28 wt %) was used as a catalyst, the amount of 1,4-DAB supplied was changed to 3.42 mmol/hr (water/DAB=3), and the reaction temperature was changed to 220° C., and the formed liquid was analyzed in the same manner to obtain the following results.

| Conversion (1,4-diacetoxybutane) | 99.7% |
| Selectivity (tetrahydrofuran) | 97.3% |

Example 8

A reaction was carried out in the same manner as in Example 1 except that 3 ml (1.34 g) of silica/zirconia (zirconia content: 5 mol %) was used as a catalyst, the amount of 1,4-DAB supplied was changed to 3.42 mmol/hr (water/DAB=3), and the reaction temperature was changed to 220° C., and the formed liquid was analyzed in the same manner to obtain the following results.

| Conversion (1,4-diacetoxybutane) | 83.8% |
| Selectivity (tetrahydrofuran) | 99.5% |

Example 9

A reaction was carried out in the same manner as in Example 1 except that 3 ml (1.78 g) of γ-alumina (manufactured by Rhone Poulenc Company, SA: 250 m$^2$/g) was used as a catalyst, the amount of 1,4-DAB supplied was changed to 3.42 mmol/hr (water/DAB=3), and the reaction temperature was changed to 260° C., and the formed liquid was analyzed in the same manner to obtain the following results.

| | |
|---|---|
| Conversion (1,4-diacetoxybutane) | 83.1% |
| Selectivity (tetrahydrofuran) | 98.2% |

Example 10

A reaction was carried out in the same manner as in Example 1 except that 5 ml (5.33 g) of titania (catalyst referred to a Catalysis Society of Japan, JRC-TiO-3, rutile type, SA: 40 m²/g) was used as a catalyst, the amount of 1,4-DAB supplied was changed to 3.46 mmol/hr (water/DAB=3), and the reaction temperature was changed to 260° C., and the formed liquid was analyzed in the same manner to obtain the following results.

| | |
|---|---|
| Conversion (1,4-diacetoxybutane) | 79.1% |
| Selectivity (tetrahydrofuran) | 98.3% |

Example 11

A reaction was carried out in the same manner as in Example 1 except that 3 ml (1.64 g) of zeolite H-ZSM-5 (manufactured by NE Chemcat Company, $SiO_2/Al_2O_3$=50) was used as a catalyst, the amount of 1,4-DAB supplied was changed to 3.46 mmol/hr (water/DAB=3), and the reaction temperature was changed to 180° C., and the formed liquid was analyzed in the same manner to obtain the following results.

| | |
|---|---|
| Conversion (1,4-diacetoxybutane) | 93.4% |
| Selectivity (tetrahydrofuran) | 95.7% |

Example 12

A reaction was carried out in the same manner as in Example 1 except that 3 ml (1.31 g) of zeolite HY (manufactured by Zeolist International Company, CBV-760, $SiO_2/Al_2O_3$=55, SA: 720 m²/g) was used as a catalyst, the amount of water supplied, was changed to 31.4 mmol/hr, and the reaction temperature was changed to 180° C., and the formed liquid was analyzed in the same manner to obtain the following results.

| | |
|---|---|
| Conversion (1,4-diacetoxybutane) | 97.1% |
| Selectivity (tetrahydrofuran) | 98.5% |

Example 13

A reaction was carried out in the same manner as in Example 1 except that 3 ml (1.21 g) of zeolite H-β (manufactured by NE Chemcat Company, $SiO_2/Al_2O_3$=25) was used as a catalyst, the amount of water supplied, was changed to 31.4 mmol/hr, and the reaction temperature was changed to 180° C., and the formed liquid was analyzed in the same manner to obtain the following results.

| | |
|---|---|
| Conversion (1,4-diacetoxybutane) | 99.6% |
| Selectivity (tetrahydrofuran) | 98.9% |

Example 14

A reaction was carried out in the same manner as in Example 1 except that 3 ml (1.51 g) of silica/titania (manufactured by Fuji Silysia Company, $TiO_2$: 5 wt %, SA: 400 m²/g) was used as a catalyst, the amount of 1,4-DAB supplied, was changed to 3.42 mmol/hr (water/DAB=3), and the reaction temperature was changed to 260° C., and the formed liquid was analyzed in the same manner to obtain the following results.

| | |
|---|---|
| Conversion (1,4-diacetoxybutane) | 21.8% |
| Selectivity (tetrahydrofuran) | 99.3% |

Example 15

A reaction was carried out in the same manner as in Example 1 except that 5 m² (3.08 g) of γ-alumina (manufactured by Rhone Poulenc Company, SA: 250 m²/g) was used as a catalyst, 4.40 mmol/hr of 1-acetoxy-4-hydroxybutane (monoester) was supplied instead of 1,4-diacetoxybutane (diester) as the reaction substrate, water was not supplied, and the reaction temperature was changed to 180° C., and the formed liquid was analyzed in the same manner to obtain the following results.

| | |
|---|---|
| Conversion (1-acetoxy-4-hydroxybutane) | 100.0% |
| Selectivity (tetrahydrofuran) | 96.5% |

Further, in the above Examples 1 to 15, the mass balance was at least about 90%.

Example 16

A reaction was carried out in the same manner as in Example 1 except that 3 ml (2.11 g) of niobic acid ($Nb_2O_5 \cdot nH_2O$, manufactured by CBMM Company, niobium hydroxide was calcined at 300° C. for two hours, the temperature raising speed: 2.5° C./min, SA: 121 m²/g) was used as a catalyst, the amount of water supplied was changed to 31.4 mmol/hr, and the reaction temperature was changed to 140° C. (under this condition, about 80 mol % of 1,4-diacetoxybutane supplied to the reaction system was vaporized), and the formed liquid was analyzed in the same manner to obtain the following results.

| | |
|---|---|
| Conversion (1,4-diacetoxybutane) | 10.2% |
| Selectivity (tetrahydrofuran) | 100% |

Further, in Examples 16, the mass balance was about 70%.

Comparative Example 1

A reaction was carried out in the same manner as in Example 16 except that the reaction temperature was changed to 120° C. (under this condition, about 30 mol % of 1,4-diacetoxybutane supplied to the reaction system was vaporized), and the formed liquid was analyzed in the same manner to obtain the following results.

| | |
|---|---|
| Conversion (1,4-diacetoxybutane) | 1.8% |
| Selectivity (tetrahydrofuran) | 100% |

Further, in the case of this condition, it was difficult to control the flow rate of the ester, and the mass balance was 76%.

The results of Examples 1 to 16 and Comparative Example 1 are shown in Table 1.

| | |
|---|---|
| (1,4-butanediol) | 0.4% |
| (monoester) | 12.0% |

Comparative Example 3

A reaction was carried out in the same manner as in Comparative Example 2 except that the reaction temperature was changed to 150° C., and the reaction liquid was analyzed in the same manner to obtain the following results. The vaporized ratio of 1,4-diacetoxybutane was at most 1 mol %.

TABLE 1

| Ex. | Water/1,4DAB (mol ratio) | Reaction temperature (° C.) | Catalyst | 1,4DAB vaporized ratio (%) | 1,4DAB conversion (%) | THF selectivity (%) | Mass balance |
|---|---|---|---|---|---|---|---|
| 1 | 1.2 | 240 | Niobic acid 1 ml (0.95 g) | 100% | 90.8 | 99.3 | At least about 90% |
| 2 | 9 | 200 | Niobic acid 3 ml (2.12 g) | | 100.0 | 99.9 | |
| 3 | 1.2 | 280 | Zirconia 4 ml (5.16 g) | | 99.9 | 99.9 | |
| 4 | 3 | 260 | Zirconia 3 ml (3.68 g) | | 97.7 | 99.6 | |
| 5 | 1.2 | 260 | Zirconia 10 ml (10.26 g) | | 96.0 | 99.9 | |
| 6 | 3 | 260 | Zirconia 5 ml (4.83 g) | | 95.5 | 96.1 | |
| 7 | 3 | 220 | Silica/alumina 3 ml (1.41 g) | | 99.7 | 97.3 | |
| 8 | 3 | 220 | Silica/zirconia 3 ml (1.34 g) | | 83.8 | 99.5 | |
| 9 | 3 | 260 | γ-alumina 3 ml (1.78 g) | | 83.1 | 98.2 | |
| 10 | 3 | 260 | Titania 5 ml (5.33 g) | | 79.1 | 98.3 | |
| 11 | 3 | 180 | Zeolite H-ZSM-5 3 ml (1.64 g) | | 93.4 | 95.7 | |
| 12 | 3.8 | 180 | Zeolite HY 3 ml (1.31 g) | | 97.1 | 98.5 | |
| 13 | 3.8 | 180 | Zeolite H-β 3 ml (1.21 g) | | 99.6 | 98.9 | |
| 14 | 3 | 260 | Silica/titania 3 ml (1.51 g) | | 21.8 | 99.3 | |
| 15* | — | 180 | γ-alumina 5 ml (3.08 g) | | 100.0 | 96.5 | |
| 16 | 3.8 | 140 | Niobic acid 3 ml (2.11 g) | About 80% | 10.2 | 100 | About 70% |
| Comp. Ex. 1 | 3.8 | 120 | Same as above | About 30% | 1.8 | 100 | 76% |

*As the reaction substrate, 1-acetoxy-4-hydroxybutane was used instead of 1,4-diacetoxybutane.

Comparative Example 2

28 mmol of 1,4-diacetoxybutane, 144 mmol of water (water/1,4-DAB=5.1), and 2 g of niobic acid ($Nb_2O_5.H_2O$, manufactured by CBMM Company) as a catalyst, were packed into a microautoclave and maintained at a reaction temperature of 120° C. for one hour in a closed system. Here, the vaporized ratio of 1,4-diacetoxybutane was at most 1 mol %. The obtained reaction liquid was analyzed by GC to obtain the following results.

| | |
|---|---|
| Conversion (1,4-diacetoxybutane) | 12.4% |
| Selectivity (tetrahydrofuran) | 0% |

| | |
|---|---|
| Conversion (1,4-diacetoxybutane) | 77.3% |
| Selectivity (tetrahydrofuran) | 1.4% |
| (1,4-butanediol) | 27.0% |
| (monoester) | 48.9% |

Comparative Example 4

A reaction was carried out in the same manner as in Comparative Example 2 except that the reaction temperature was changed to 180° C., and the reaction liquid was analyzed in the same manner to obtain the following results. The vaporized ratio of 1,4-diacetoxybutane was at most 1 mol %.

| | |
|---|---|
| Conversion (1,4-diacetoxybutane) | 79.3% |
| Selectivity (tetrahydrofuran) | 12.2% |
| (1,4-butanediol) | 19.5% |
| (monoester) | 47.6% |

Comparative Example 5

A reaction was carried out in the same manner as in Comparative Example 2 except that 1,4-diacetoxybutane was changed to 56 mmol, water was changed to 289 mmol (water/1,4-DAB=5.2), and the catalyst niobic acid was changed to 0.25 g, and the reaction liquid was analyzed in the same manner to obtain the following results. The vaporized ratio of 1,4-diacetoxybutane was at most 1 mol %.

| | |
|---|---|
| Conversion (1,4-diacetoxybutane) | 75.6% |
| Selectivity (tetrahydrofuran) | 1.7% |
| (1,4-butanediol) | 23.5% |
| (monoester) | 50.4% |

Further, this catalyst was repeatedly used to carry out the reaction, and the reaction liquid was analyzed in the same manner to obtain the following results.

Repeated number of times: twice

| | |
|---|---|
| Conversion (1,4-diacetoxybutane) | 46.9% |
| Selectivity (tetrahydrofuran) | 0% |
| (1,4-butanediol) | 6.2% |
| (monoester) | 40.7% |

Repeated number of times: three times

| | |
|---|---|
| Conversion (1,4-diacetoxybutane) | 25.6% |
| Selectivity (tetrahydrofuran) | 0% |
| (1,4-butanediol) | 1.1% |
| (monoester) | 24.4% |

Comparative Example 6

A reaction was carried out in the same manner as in Comparative Example 2 except that 1 g of zirconia (manufactured by Norton Company, SA: 335 m²/g) was used as a catalyst, and the reaction temperature was changed to 200° C., and the reaction liquid was analyzed in the same manner to obtain the following results. The vaporized ratio of 1,4-diacetoxybutane was at most 1 mol %.

| | |
|---|---|
| Conversion (1,4-diacetoxybutane) | 72.8% |
| Selectivity (tetrahydrofuran) | 1.8% |
| (1,4-butanediol) | 21.9% |
| (monoester) | 49.1% |

Comparative Example 7

A reaction was carried out in the same manner as in Comparative Example 6 except that the reaction temperature was changed to 220° C., and the reaction liquid was analyzed in the same manner to obtain the following results. The vaporized ratio of 1,4-diacetoxybutane was at most 1 mol %.

| | |
|---|---|
| Conversion (1,4-diacetoxybutane) | 76.4% |
| Selectivity (tetrahydrofuran) | 4.2% |
| (1,4-butanediol) | 20.5% |
| (monoester) | 51.6% |

The results of Comparative Examples 2 to 7 are shown in Table 2.

TABLE 2

| Comp. Ex. | Water/1,4DAB (mol ratio) | Reaction temperature (° C.) | Catalyst | 1,4DAB vaporized ratio (%) | 1,4DAB conversion (%) | THF selectivity (%) |
|---|---|---|---|---|---|---|
| 2 | 5.1 | 120 | Niobic acid | At most | 12.4 | 0 |
| 3 | | 150 | (2 g) | 1 mol % | 77.3 | 1.4 |
| 4 | | 180 | | | 79.3 | 12.2 |
| 5 | 5.2 | 120 | Niobic acid (0.25 g) | | 75.6 | 1.7 |
| 6 | 5.1 | 200 | Zirconia | | 72.8 | 1.8 |
| 7 | | 220 | (1 g) | | 76.4 | 4.2 |

Comparative Examples 2 to 7 represent cases wherein the reaction was carried out in such a state that at least 99 mol % of 1,4-diacetoxybutane was liquefied, whereby it is evident that even if the reaction was carried out as long as one hour, the conversion of 1,4-diacetoxybutane and the selectivity for tetrahydrofuran were low, and the majority of the product was monoester as an intermediate product of hydrolysis. Further, from Comparative Example 5, it is apparent that by the repeated use of the catalyst, the conversion of 1,4-diacetoxybutane and the selectivity for tetrahydrofuran decreased.

On the other hand, it is apparent that in Examples 1 to 16, the reaction was carried out in such a state that at least 50 mol % of the ester as a reaction substrate was vaporized, whereby even if the reaction time is in the order of seconds, the conversion of 1,4-diacetoxybutane and the selectivity for tetrahydrofuran were remarkably high, and there is a merit in that the reaction can be carried out within a wide reaction temperature range from a low temperature (140° C.) to a high temperature (280° C.).

Further, from Example 15, it is apparent that when the raw material ester is all monoester, even if no water is supplied, THF can be produced in high yield. Further, from Examples 1, 3 and 5, it is apparent that even if the amount of water is decreased to a level of substantially 1 time by mol to the equivalent of the difatty acid ester of 1,4-butanediol, THF can be produced in good yield, and water remaining after the reaction can be minimized.

INDUSTRIAL APPLICABILITY

According to the process of the present invention, the conversion of tetrahydrofuran can be improved, and the reaction can be carried out within a wide reaction temperature range of from a low temperature to a high temperature, as compared with the conventional liquid phase reaction or the gas/liquid mixed reaction, and formation of by-products (such as 3-butene-1-ol and 4-acetoxy-1-butene) can be reduced. Further, there will be merits such that it is easy to control the flow rate or the contact time, no deterioration of the catalyst occurs even in a reaction at a high temperature or for a long period of time, and the production can be carried out constantly in high yield over a long period of time. Further, when a diester is used as the raw material ester, the amount of water can be reduced to a level of substantially 1 time by mol to the equivalent of the difatty acid ester of the $\alpha$, $\delta$-diol, and the cyclic ether can be produced in high yield, and water remaining after the reaction can be minimized, whereby there will be a merit in that the load in the subsequent separation between water and the product can be reduced. Further, a corrosive liquid acid such as sulfuric acid is not employed, whereby there is a merit in that it is not necessary to employ a high grade material of the reactor.

The entire disclosures of Japanese Patent Application No. 2000-176303 filed on Jun. 13, 2000 and Japanese Patent Application No. 2000-189193 filed on Jun. 23, 2000 including specifications, claims and summaries are incorporated herein by reference in their entireties.

What is claimed is:

1. A process for producing a saturated cyclic ether, which comprises reacting a mono- and/or di-fatty acid ester of an $\alpha$, $\delta$-diol in the presence of a solid acid catalyst, wherein the reaction is carried out in such a state that at least 50 mol % of the fatty acid ester supplied to the reaction system is vaporized and wherein the amount of water supplied is adjustable to be at most 5 times by mol to the amount of the fatty acid ester supplied.

2. The process for producing a saturated cyclic ether according to claim 1, wherein the reaction is carried out in such a state that at least 70 mol % of the fatty acid ester supplied to the reaction system is vaporized.

3. The process for producing a saturated cyclic ether according to claim 1, wherein the reaction is carried out in the presence of water.

4. The process for producing a saturated cyclic ether according to claim 3, wherein the reaction is carried out in such a state that substantially all of the fatty acid ester and water are vaporized.

5. The process for producing a saturated cyclic ether according to claim 1, wherein the fatty acid ester is supplied to the reaction system in such a state that at least 50 mol % thereof is preliminarily vaporized.

6. The process for producing a saturated cyclic ether according to claim 5, wherein substantially all of the fatty acid ester is supplied in a vaporized state to the reaction system.

7. The process for producing a saturated cyclic ether according to claim 1, wherein the reaction is carried out under such a condition that the molar ratio of raw material components to be introduced into the reaction system, and the saturated vapor pressure of the fatty acid ester at the reaction temperature under the reaction pressure, satisfy the following relation:

(mols corresponding to 50 mol % of the fatty acid ester/total mols of all materials)<(saturated vapor pressure of the fatty acid ester at the reaction temperature under the reaction pressure/reaction pressure)

where all materials mean the fatty acid ester, water and gaseous inert components.

8. The process for producing a saturated cyclic ether according to claim 7, wherein the reaction is carried out under such a condition that the molar ratio of raw material components to be introduced into the reaction system, and the saturated vapor pressure of the fatty acid ester at the reaction temperature under the reaction pressure, satisfy the following relation:

(mols corresponding to 70 mol % of the fatty acid ester/total mols of all materials)<(saturated vapor pressure of the fatty acid ester at the reaction temperature under the reaction pressure/reaction pressure)

where all materials mean the fatty acid ester, water and gaseous inert components.

9. The process for producing a saturated cyclic ether according to claim 1, wherein the reaction is carried out at a reaction temperature higher than the boiling point of the fatty acid ester under the actual reaction pressure.

10. The process for producing a saturated cyclic ether according to claim 1, wherein a gaseous inert component inert to the reaction is added.

11. The process for producing a saturated cyclic ether according to claim 1, wherein the reaction pressure is not higher than atmospheric pressure.

12. The process for producing a saturated cyclic ether according to claim 1, wherein a fatty acid ester of 1,4-butanediol is reacted to produce tetrahydrofuran.

13. The process for producing a saturated cyclic ether according to claim 1, wherein the fatty acid ester is a di-fatty acid ester of an $\alpha$, $\delta$-diol.

14. The process for producing a saturated cyclic ether according to claim 1, wherein the fatty acid ester is a mono-fatty acid ester of an $\alpha$, $\delta$-diol.

15. The process for producing a saturated cyclic ether according to claim 1, wherein the solid acid catalyst is niobic acid or zirconia.

* * * * *